US006595934B1

(12) United States Patent
Hissong et al.

(10) Patent No.: US 6,595,934 B1
(45) Date of Patent: *Jul. 22, 2003

(54) METHODS OF SKIN REJUVENATION USING HIGH INTENSITY FOCUSED ULTRASOUND TO FORM AN ABLATED TISSUE AREA CONTAINING A PLURALITY OF LESIONS

(75) Inventors: James B. Hissong, Jacksonville, FL (US); Fred B. Dinger, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 284 days.

This patent is subject to a terminal disclaimer.

(21) Appl. No.: 09/629,194

(22) Filed: Jul. 31, 2000

Related U.S. Application Data

(63) Continuation-in-part of application No. 09/487,705, filed on Jan. 19, 2000, now abandoned.

(51) Int. Cl.[7] .............................................. A61B 18/04
(52) U.S. Cl. ................................ 601/3; 606/27; 606/28
(58) Field of Search ..................... 601/2–4; 600/439; 607/50; 606/31, 28

(56) References Cited

U.S. PATENT DOCUMENTS

| | | |
|---|---|---|
| 3,990,452 A | 11/1976 | Murry et al. |
| 4,508,122 A | 4/1985 | Gardineer et al. |
| 4,658,828 A | 4/1987 | Dory |
| 4,807,633 A | 2/1989 | Fry |
| 4,858,613 A | 8/1989 | Fry et al. |
| 4,917,096 A | 4/1990 | Engelhart et al. |
| 4,951,653 A | 8/1990 | Fry et al. |
| 4,955,365 A | 9/1990 | Fry et al. |
| RE33,590 E | 5/1991 | Dory |
| 5,033,456 A | 7/1991 | Pell et al. |

(List continued on next page.)

FOREIGN PATENT DOCUMENTS

| | | |
|---|---|---|
| WO | WO97/43970 | 11/1997 |

OTHER PUBLICATIONS

Company Press Release—FDA Clears First–of–its–Kind Device for Treatment of Sleep Disorder Affecting 20 Million Americans, 4pgs, Nov. 5, 1998.

(List continued on next page.)

*Primary Examiner*—Ruth S. Smith

(57) ABSTRACT

A method of skin rejuvenation by thermal ablation using high intensity focused ultrasound energy includes the steps of positioning an ultrasound emitting member adjacent an external surface of the skin, emitting ultrasound energy from the ultrasound emitting member into the skin, focusing the ultrasound energy in the skin, ablating the skin with the focused ultrasound energy to form an ablated tissue area below the external surface of the skin containing unablated tissue of the skin and a plurality of lesions at which the tissue of the skin is ablated, and removing the ultrasound emitting member from adjacent the external surface of the skin. The lesions cause collagen production by the skin to be stimulated. The lesions can begin and end at predetermined depths beneath the external surface of the skin so that the epidermis and the deep layer of the dermis are not damaged.

18 Claims, 2 Drawing Sheets

U.S. PATENT DOCUMENTS

| | | |
|---|---|---|
| 5,036,855 A | 8/1991 | Fry et al. |
| 5,054,470 A | 10/1991 | Fry et al. |
| 5,065,761 A | 11/1991 | Pell |
| 5,080,101 A | 1/1992 | Dory |
| 5,080,102 A | 1/1992 | Dory |
| 5,117,832 A | 6/1992 | Sanghvi et al. |
| 5,134,988 A | 8/1992 | Pell et al. |
| 5,143,074 A | 9/1992 | Dory |
| 5,150,711 A | 9/1992 | Dory |
| 5,150,712 A | 9/1992 | Dory |
| 5,158,070 A | 10/1992 | Dory |
| 5,222,501 A | 6/1993 | Ideker et al. |
| 5,247,935 A | 9/1993 | Cline et al. |
| 5,267,954 A | 12/1993 | Nita |
| 5,269,291 A | 12/1993 | Carter |
| 5,269,297 A | 12/1993 | Weng et al. |
| 5,295,484 A | 3/1994 | Marcus et al. |
| 5,304,115 A | 4/1994 | Pflueger et al. |
| 5,312,328 A | 5/1994 | Nita et al. |
| 5,318,014 A | 6/1994 | Carter |
| 5,342,292 A | 8/1994 | Nita et al. |
| 5,354,258 A | 10/1994 | Dory |
| 5,380,274 A | 1/1995 | Nita |
| 5,391,197 A | 2/1995 | Burdette |
| 5,397,301 A | 3/1995 | Pflueger et al. |
| 5,409,002 A | 4/1995 | Pell |
| 5,417,672 A | 5/1995 | Nita et al. |
| 5,423,812 A | 6/1995 | Ellman et al. |
| 5,431,621 A | 7/1995 | Dory |
| 5,431,663 A | 7/1995 | Carter |
| 5,447,509 A | 9/1995 | Miller et al. |
| 5,456,662 A | 10/1995 | Edwards |
| 5,474,530 A | 12/1995 | Passafaro et al. |
| 5,492,126 A | 2/1996 | Hennige et al. |
| 5,501,655 A | 3/1996 | Rolt et al. |
| 5,514,131 A | 5/1996 | Edwards |
| 5,520,188 A | 5/1996 | Hennige et al. |
| 5,542,917 A | 8/1996 | Nita et al. |
| 5,620,479 A | 4/1997 | Diederich |
| 5,624,439 A | 4/1997 | Edwards |
| 5,674,191 A | 10/1997 | Edwards |
| 5,676,692 A | 10/1997 | Sanghvi et al. |
| 5,707,349 A | 1/1998 | Edwards |
| 5,718,702 A | 2/1998 | Edwards |
| 5,720,719 A | 2/1998 | Edwards et al. |
| 5,728,094 A | 3/1998 | Edwards |
| 5,730,719 A | 3/1998 | Edwards |
| 5,733,315 A | 3/1998 | Burdette et al. |
| 5,735,280 A | 4/1998 | Sherman et al. |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,762,066 A | 6/1998 | Law et al. |
| 5,800,379 A | 9/1998 | Edwards |
| 5,800,429 A | 9/1998 | Edwards |
| 5,800,482 A | 9/1998 | Pomeranz et al. |
| 5,807,308 A | 9/1998 | Edwards |
| 5,817,049 A | 10/1998 | Edwards |
| 5,823,197 A | 10/1998 | Edwards |
| 5,827,277 A | 10/1998 | Edwards |
| 5,843,077 A | 12/1998 | Edwards |
| 5,871,524 A | 2/1999 | Knowlton |
| 5,873,845 A | 2/1999 | Cline et al. |
| 5,873,902 A | 2/1999 | Sanghvi et al. |
| 5,879,349 A | 3/1999 | Edwards |
| 5,882,302 A | 3/1999 | Driscoll, Jr. et al. |
| 5,895,356 A | 4/1999 | Andrus et al. |
| 5,928,169 A * | 7/1999 | Schatzle et al. ............... 601/2 |
| 5,938,608 A | 8/1999 | Bieger et al. |
| 5,984,881 A | 11/1999 | Ishibashi et al. |
| 5,984,882 A | 11/1999 | Rosenschein et al. |
| 6,007,499 A | 12/1999 | Martin et al. |
| 6,026,816 A | 2/2000 | McMillan et al. |
| 6,096,033 A | 8/2000 | Tu et al. |
| 6,113,559 A * | 9/2000 | Klopotek ........................ 601/3 |
| 6,126,657 A * | 10/2000 | Edwards et al. ............... 606/45 |
| 6,135,971 A | 10/2000 | Hutchinson et al. |
| 6,174,280 B1 | 1/2001 | Oneda et al. |
| 6,190,381 B1 | 2/2001 | Olsen et al. |
| 6,210,355 B1 | 4/2001 | Edwards et al. |
| 6,217,530 B1 | 4/2001 | Martin et al. |
| 6,241,753 B1 | 6/2001 | Knowlton |
| 6,309,355 B1 | 10/2001 | Cain et al. |
| 6,325,769 B1 | 12/2001 | Klopotek |
| 6,361,531 B1 * | 3/2002 | Hissong ........................ 606/27 |
| 6,409,720 B1 * | 6/2002 | Hissong et al. ............... 606/27 |
| 6,413,254 B1 * | 7/2002 | Hissong et al. ............... 606/27 |
| 6,451,013 B1 * | 9/2002 | Bays et al. .................... 606/27 |

OTHER PUBLICATIONS

Clinical Investigations—Radiofrequency Volumetric Tissue Reduction of the Palate in Subjects with Sleep–Disordered Breathing, Nelson B. Powell, MD; Robert W. Rile, DDS, MD; Robert J. Troell, MD; Kasey Li, MD; Marc B. Blumen, MD; Christian Guilleminault, MD, 12 pages, May 5, 1998.

Somnoplasty for Obstructive Sleep Apnea, 1 page, http:/www.somnus.com/som/osa.htm, Jan. 6, 1999.

Somnoplasty For the Treatment of Snoring, 2 pgs, http:/www.somnus.com/som.snor.htm, Jan. 6, 1999.

Sonablate Technology with HIFU, 2 pages, http:www.focus–surgery.com/tech.html, Feb. 17, 1999.

Focus Surgery, (McDonald & Company), 1 page, Feb. 23, 1999.

Laboratory and animal investigations—Radiofrequency Volumetric Reduction of the Tongue, Nelson B. Powell, MD; Robert W. Riley, MD; Robert J. Troell, MD; Marc B. Blumen, MD; Christian Guilleminault, MD, 8 pages, May 5, 1997.

* cited by examiner

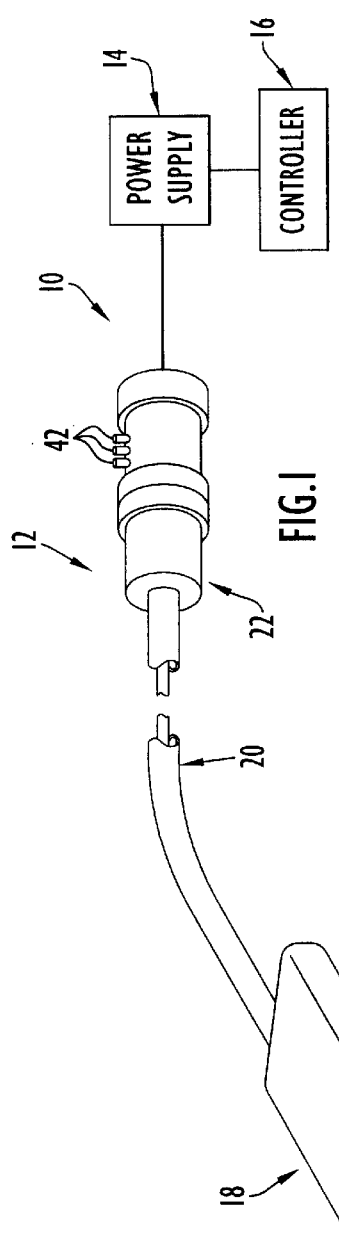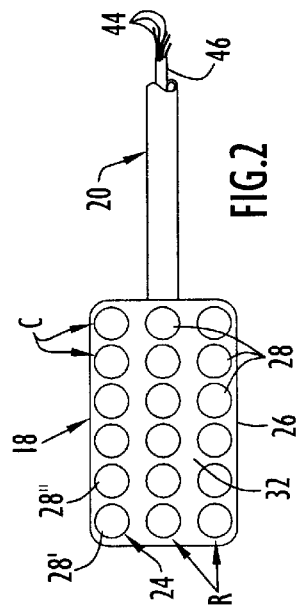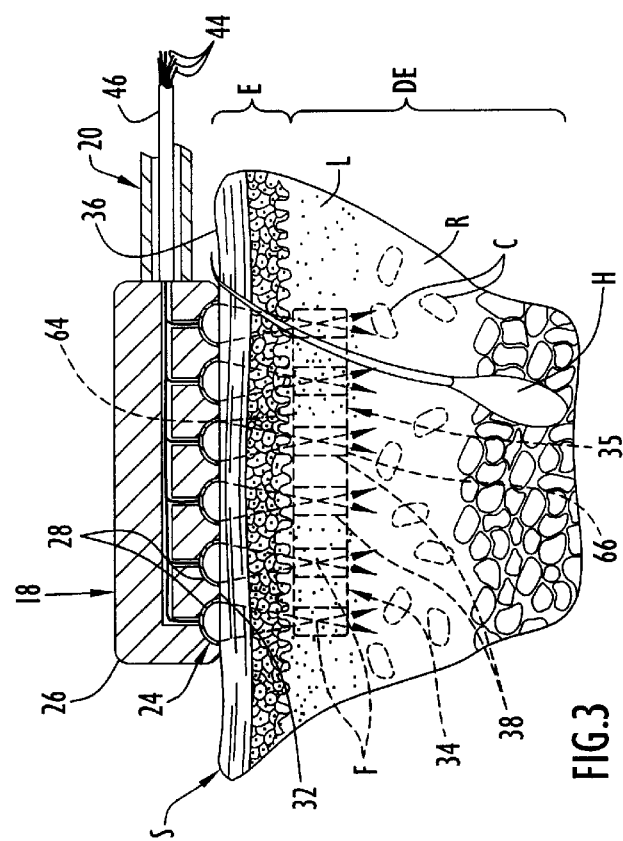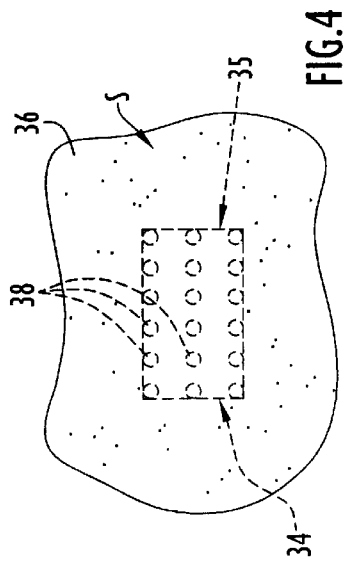

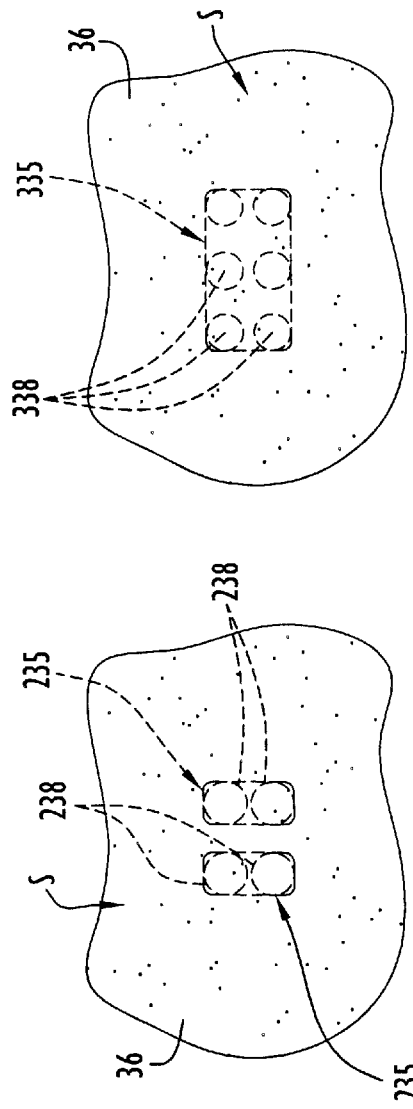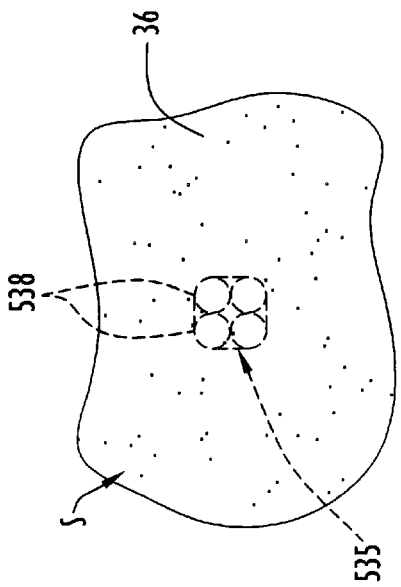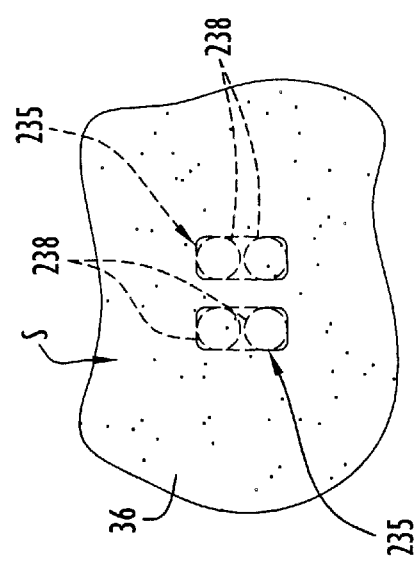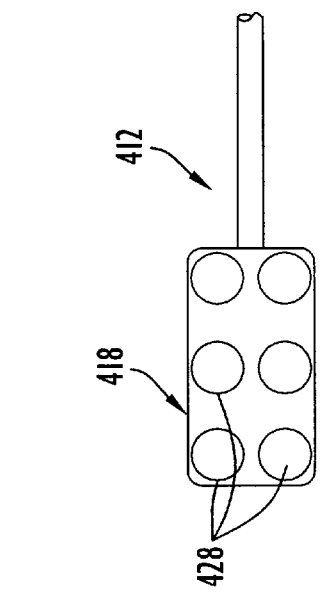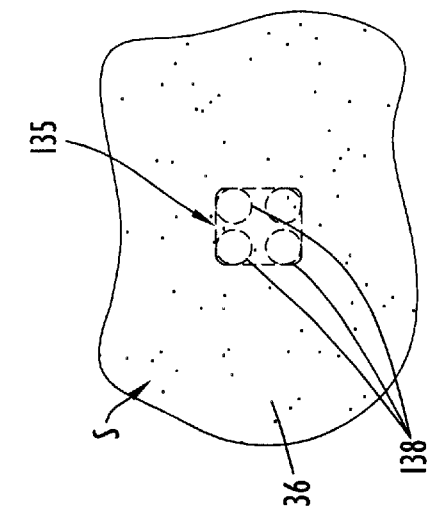

METHODS OF SKIN REJUVENATION USING HIGH INTENSITY FOCUSED ULTRASOUND TO FORM AN ABLATED TISSUE AREA CONTAINING A PLURALITY OF LESIONS

CROSS-REFERENCE TO RELATED PATENT APPLICATIONS

This application is a continuation-in-part of prior U.S. patent application Ser. No. 09/487,705 filed Jan. 19, 2000 now abandoned, the disclosure of which is incorporated herein by reference.

This application is related to U.S. patent applications Ser. No. 09/487,708 filed Jan. 19, 2000 now abandoned, and entitled Methods of Soft Palate Reduction By Thermal Ablation Using High Intensity Focused Ultrasound, Ser. No. 09/487,707 filed Jan. 19, 2000 and entitled Methods of Tongue Reduction By Thermal Ablation Using High Intensity Focused Ultrasound now U.S. Pat. No. 6,413,254 issued Jul. 2, 2002, Ser. No. 09/487,709 filed Jan. 19, 2000 and entitled Methods of Tonsil Reduction By Thermal Ablation Using High Intensity Focused Ultrasound now abandoned, Ser. No. 09/487,706 filed Jan. 19, 2000 and entitled Methods of Turbinate Or Other Soft Tissue Reduction By Thermal Ablation Using High Intensity Focused Ultrasound now abandoned, Ser. No. 09/488,844 filed Jan. 21, 2000 and entitled Focused Ultrasound Ablation Devices Having Malleable Handle Shafts and Methods of Using the Same now U.S. Pat. No. 6,361,531 issued Mar. 26, 2002, and Ser. No. 09/487,710 filed Jan. 19, 2000 and entitled Focused Ultrasound Ablation Devices Having Selectively Actuatable Ultrasound Emitting Elements and Methods of Using the Same, the disclosures of which are incorporated herein by reference.

This application is also related to co-pending U.S. patent applications entitled Methods of Soft Palate Reduction Using High Intensity Focused Ultrasound To Form An Ablated Tissue Area Containing A Plurality of Lesions, Methods of Tongue Reduction Using High Intensity Focused Ultrasound To Form An Ablated Tissue Area Containing A Plurality of Lesions, Methods of Tonsil Reduction Using High Intensity Focused Ultrasound To Form An Ablated Tissue Area Containing A Plurality of Lesions and Methods of Turbinate Or Other Soft Tissue Reduction Using High Intensity Focused Ultrasound To Form An Ablated Tissue Area Containing A Plurality of Lesions, the disclosures of which are incorporated herein by reference.

BACKGROUND OF THE INVENTION

1. Field of the Invention

The present invention relates generally to the treatment of anatomical tissue of the head and/or neck with high intensity focused ultrasound energy and, more particularly, to skin rejuvenation by thermal stimulation using high intensity focused ultrasound.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. In order to produce thermal effects in anatomical tissue, ultrasound emitting members such as transducers have been used to emit ultrasound energy which is applied to anatomical tissue by positioning the ultrasound emitting members adjacent or in contact with the tissue or by coupling the ultrasound emitting members to the tissue via an acoustic coupling medium. By focusing the ultrasound energy at one or more specific focusing zones within the tissue, thermal effects can be confined to a defined location, region, volume or area, and such location, region, volume or area can be remote from the ultrasound emitting member.

With the use of high intensity focused ultrasound (HIFU), one or more focusing zones at or within a designated target location, region, volume or area within a larger mass, body or area of anatomical tissue can be subjected to high intensity ultrasound energy while tissue surrounding the target area is subjected to much lower intensity ultrasound energy. In this manner, tissue in the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue in a target location, volume, region or area to an ablative temperature creates an ablative lesion in the tissue in the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of high intensity focused ultrasound to eliminate tissue or to alter the characteristics of tissue in a target location, volume, region or area within a larger mass, body or area of anatomical tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various devices and/or methods for treating anatomical tissue with ultrasound have been proposed as represented by U.S. Pat. No. Re. 33,590 to Dory, U.S. Pat. No. 3,990,452 to Murry et al, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,033,456 to Pell et al, U.S. Pat. No. 5,036,855 to Fry et al, U.S. Pat. No. 5,054,470 to Fry et al, U.S. Pat. No. 5,065,761 to Pell, U.S. Pat. No. 5,080,101 to Dory, U.S. Pat. No. 5,080,102 to Dory, U.S. Pat. No. 5,117,832 to Sanghvi et al, U.S. Pat. No. 5,134,988 to Pell et al, U.S. Pat. No. 5,143,074 to Dory, U.S. Pat. No. 5,150,711 to Dory, No. 5,150,712 to Dory, U.S. Pat. No. 5,158,070 to Dory, U.S. Pat. No. 5,222,501 to Ideker et al, U.S. Pat. No. 5,267,954 to Nita, U.S. Pat. No. 5,269,291 to Carter, U.S. Pat. No. 5,269,297 to Weng et al, U.S. Pat. No. 5,295,484 to Marcus et al, U.S. Pat. No. 5,304,115 to Pflueger et al, U.S. Pat. No. 5,312,328 to Nita et al, U.S. Pat. No. 5,318,014 to Carter, U.S. Pat. No. 5,342,292 to Nita et al, U.S. Pat. No. 5,354,258 to Dory, U.S. Pat. No. 5,380,274 to Nita, U.S. Pat. No. 5,391,197 to Burdette et al, U.S. Pat. No. 5,397,301 to Pflueger et al, U.S. Pat. No. 5,409,002 to Pell, U.S. Pat. No. 5,417,672 to Nita et al, U.S. Pat. No. 5,431,621 to Dory, U.S. Pat. No. 5,431,663 to Carter, U.S. Pat. No. 5,447,509 to Mills et al, U.S. Pat. No. 5,474,530 to Passafaro et al, U.S. Pat. No. 5,492,126 to Hennige et al, U.S. Pat. No. 5,501,655 to Rolt et al, U.S. Pat. No. 5,520,188 to Hennige et al, U.S. Pat. No. 5,542,917 to Nita et al, U.S. Pat. No. 5,620,479 to Diederich, U.S. Pat. No. 5,676,692 to Sanghvi et al, U.S. Pat. No. 5,728,094 to Edwards, U.S. Pat. No. 5,730,719 to Edwards, U.S. Pat. No. 5,733,315 to Burdette et al, U.S. Pat. No. 5,735,280 to Sherman et al, U.S. Pat. No. 5,738,114 to Edwards, U.S. Pat. No. 5,746,224 to Edwards, U.S. Pat. No. 5,762,066 to Law et al, U.S. Pat. No. 5,800,379 to Edwards, U.S. Pat. No. 5,800,429 to Edwards, U.S. Pat. No. 5,800,482 to Pomeranz et al, U.S. Pat. No. 5,807,308 to Edwards, U.S. Pat. No. 5,817,049 to Edwards, U.S. Pat. No. 5,823,197 to Edwards, U.S. Pat. No. 5,827,277 to Edwards, U.S. Pat. No. 5,843,077 to Edwards, U.S. Pat. No. 5,871, 524 to Knowlton, U.S. Pat. No. 5,873,845 to Cline et al, U.S. Pat. No. 5,873,902 to Sanghvi et al, U.S. Pat. No. 5,879,349 to Edwards, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al.

In particular, the use of high intensity focused ultrasound to thermally damage, ablate, coagulate, denature, cauterize, necrotize or destroy a target volume of tissue is exemplified by U.S. Pat. No. Re. 33,590 to Dory, U.S. Pat. No. 4,658,828 to Dory, U.S. Pat. No. 4,807,633 to Fry, U.S. Pat. No. 4,858,613 to Fry et al, U.S. Pat. No. 4,951,653 to Fry et al, U.S. Pat. No. 4,955,365 to Fry et al, U.S. Pat. No. 5,036,855 to Fry et al, U.S. Pat. No. 5,054,470 to Fry et al, U.S. Pat. No. 5,080,101 to Dory, U.S. Pat. No. 5,080,102 to Dory, U.S. Pat. No. 5,117,832 to Sanghvi et al, U.S. Pat. No. 5,143,074 to Dory, U.S. Pat. No. 5,150,711 to Dory, U.S. Pat. No. 5,150,712 to Dory, U.S. Pat. No. 5,295,484 to Marcus et al, U.S. Pat. No. 5,354,258 to Dory, U.S. Pat. No. 5,391,197 to Burdette et al, U.S. Pat. No. 5,431,621 to Dory, U.S. Pat. No. 5,492,126 to Hennige et al, U.S. Pat. No. 5,501,655 to Rolt et al, U.S. Pat. No. 5,520,188 to Hennige et al, U.S. Pat. No. 5,676,692 to Sanghvi et al, U.S. Pat. No. 5,733,315 to Burdette et al, U.S. Pat. No. 5,762,066 to Law et al, U.S. Pat. No. 5,871,524 to Knowlton, U.S. Pat. No. 5,873,845 to Cline et al, U.S. Pat. No. 5,873,902 to Sanghvi et al, U.S. Pat. No. 5,882,302 to Driscoll, Jr. et al, U.S. Pat. No. 5,895,356 to Andrus et al, U.S. Pat. No. 5,928,169 to Schätzle et al and U.S. Pat. No. 5,938,608 to Bieger et al.

The skin is the largest organ of the body and is highly vulnerable to deterioration due to natural aging and/or exposure to environmental conditions such as sun, wind, heat and cold. The skin includes two primary layers, i.e. the epidermis and the dermis. The epidermis is the outermost layer of the skin and presents a barrier to deter the entry of UV radiation, germs, heat, cold, dirt and gases while deterring the egress of water, blood, minerals, vitamins, hormones and protein. The epidermis is composed of a plurality of sub-layers including several layers of stratified epithelial tissue. The basilar layer of the epidermis includes melanocytes and other epithelial cells. Melanin is produced by the melanocytes and serves to protect the skin from harmful effects of ultraviolet radiation. Skin cells are continuously moving from the lower layers to the upper layers of the epidermis and are sloughed off after they reach the skin surface. The dermis is comprised of dense, irregular connective tissue and contains blood vessels, sweat glands, sebaceous glands, nerves, collagen and elastin. Collagen contributes to the firmness of the skin, and elastin imparts flexibility and durability to the skin. The potential outcome of increased collagen levels in facial skin is a reduction of wrinkles with enhanced skin resilience and a more youthful appearance.

There is a great demand for methods or procedures to reduce the effects of aging and/or environmental exposure in skin and, in particular, facial skin. Conventional techniques for removing facial wrinkles include cosmetic or plastic surgery, one technique being commonly known as "skin resurfacing". Cosmetic surgery has numerous drawbacks including invasiveness, trauma, scarring, pain, significant recovery times and high financial cost. Conventional, non-surgical techniques for removing facial wrinkles involve destruction of the epidermis and/or dermis by laser energy used to vaporize the tissue, chemical burns or peels, physical debridement using drills and blasting the skin with a pressurized stream of beads. Such non-surgical techniques typically destroy the epidermis, resulting in temporary and possibly permanent impairment of the skin. For example, patients may be left with various pigmentation problems including blotchiness, a predominantly white complexion and/or the inability to tan.

U.S. Pat. No. 5,743,904 to Edwards discloses RF ablation of body structures, including fatty tissues in the cheeks, jaw and near the eyes, via electrodes inserted in the tissue. U.S. Pat. No. 5,871,524 to Knowlton discloses the use of RF electrodes and an electrolytic solution to create a reverse thermal gradient in the skin to effect partial denaturation and shrinkage of collagen resulting in tightening of the skin. Ultrasound is alluded to as a possible source of radiant energy to create the reverse thermal gradient. The stimulation of collagen growth by delivery of energy into the superficial layers of the dermis has also been recognized. Lasers having wavelengths that penetrate the epidermis without damage thereto and stimulate the dermis to create collagen are being developed and marketed.

It has not been previously recognized to thermally stimulate collagen growth by delivery of focused ultrasound energy into superficial layers of the dermis, while avoiding damage to the epidermis, in a minimally invasive, non-traumatic procedure not requiring physical penetration or wounding of the skin and while confining thermal stimulation to a specific target area or areas within the skin.

SUMMARY OF THE INVENTION

Accordingly, it is a primary object of the present invention to overcome the various disadvantages of prior methods of skin rejuvenation.

It is also an object of the present invention to effect skin rejuvenation by using high intensity focused ultrasound to stimulate collagen growth.

Another object of the present invention is to utilize high intensity focused ultrasound to effect wrinkle reduction by increasing collagen levels in skin.

It is also an object of the present invention to use high intensity focused ultrasound to thermally stimulate collagen growth in skin without impairing the epidermis.

The present invention also has as an object to use high intensity focused ultrasound to thermally stimulate superficial layers of the dermis to increase collagen growth without damaging the epidermis.

Still a further object of the present invention is to focus ultrasound energy within the skin to form an internal ablated tissue area beginning a predetermined distance beneath an external surface of the skin in order to stimulate collagen production.

The present invention also has as an object to focus ultrasound energy, emitted by an ultrasound emitting member, within the skin to form an internal ablated tissue area beginning a predetermined distance from an active face of the ultrasound emitting member in order to stimulate collagen production.

It is another object of the present invention to use high intensity focused ultrasound to form an ablated tissue area in the skin to a predetermined depth so that deep layers of the skin are not damaged.

An additional object of the present invention is to focus ultrasound energy within the skin to form an ablated tissue area in the superficial layer of the dermis but not the deep layer of the dermis.

Some of the advantages of the present invention are that varying intensity levels of ultrasound energy can be delivered to the skin for varying periods of time depending on desired ablative effect, the duration of ultrasound energy delivery or application to the skin needed to accomplish a desired stimulation may be relatively brief depending on desired size for the lesions of the ablated tissue area and/or desired thermal effect on the tissue, the transducer or other member used to emit the ultrasound energy may be stationary or may be movable in order to scan a target area with focused ultrasound, a plurality of individual ablated tissue areas can be formed in the skin with the ablated tissue areas being separate and discontinuous or being contacting, abutting, contiguous or overlapping to form a single continuous ablated tissue area of desired size and/or shape, the ultrasound emitting member can remain stationary or can be moved along the skin to scan a target area with focused ultrasound, the transducer or other member may be designed with a focusing configuration designed to ensure that the lesions of the ablated tissue area have a desired cross-sectional size, begin a desired depth within the skin and have a desired depth, the superficial dermis is thermally damaged to stimulate collagen growth with minimal trauma and pain for the patient, the transducer or other member is positioned externally adjacent or in contact with an external surface of the skin or is acoustically coupled with the skin to form an internal ablated tissue area without damaging the external skin surface and, in particular, the epidermis, no external wound is presented since the epidermis is preserved, and an ablated tissue area of definitive size can be repeatedly and consistently produced.

These and other objects, advantages and benefits are realized with the present invention as generally characterized in a method of skin rejuvenation or wrinkle reduction by thermal stimulation using high intensity focused ultrasound wherein an ultrasound emitting member is positioned adjacent an external surface of the skin, and ultrasound energy is emitted from the ultrasound emitting member into the tissue of the skin. The ultrasound energy is focused within the skin at a plurality of focusing zones disposed beneath the external skin surface and contained in a target area coincident with or containing the superficial dermis. The focusing zones are spaced from one another and, due to focusing of the ultrasound energy at the focusing zones, the ultrasound energy is of higher or greater intensity in the tissue at the focusing zones than in the tissue surrounding the focusing zones. The tissue of the skin is heated at the focusing zones by the focused ultrasound energy, thereby forming an ablated tissue area below the external skin surface containing unablated skin tissue and a plurality of lesions at the focusing zones, respectively, at which the tissue of the skin is ablated. Once an ablated tissue area of desired extent has been obtained in the skin, the ultrasound emitting member is removed. In reaction to the lesions, natural production of collagen in the dermis is stimulated. Collagen levels in the skin are thusly increased, resulting in a reduction of wrinkles and enhanced skin resilience for a more youthful appearance.

The ultrasound emitting member has a focusing configuration causing the ultrasound energy to be focused a predetermined distance from an active face of the ultrasound emitting member and, therefore, from the external surface of the skin, so that the epidermis is undamaged and preserved. Also, the focusing configuration results in formation of lesions of predetermined or known depth in accordance with the length of the focusing zones, the selected ultrasound energy intensities and the selected duration times for ultrasound energy delivery. The lesion depths are selected so that the lesions do not extend deeper than desired in the skin, thereby avoiding damage to the deep layer of the dermis. The plurality of lesions may be non-contacting, with each lesion surrounded by unablated skin tissue. One or more of the plurality of lesions may contact another one of the plurality of lesions. The cross-sectional size of the lesions and the location and arrangement of the focusing zones in the skin result in formation of a specific size ablated tissue area having a specific cross-sectional configuration. A single, discrete ablated tissue area or a plurality of single, discrete ablated tissue areas can be formed in the skin in a single procedure or treatment performed at one time or in multiple procedures or treatments performed at different times. Where a plurality of ablated tissue areas are formed, the ablated tissue areas can be contiguous, contacting, overlapping or in abutment with one another so that the ablated tissue areas together form or create a single ablated tissue area of larger cross-sectional size and/or of a desired cross-sectional configuration.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 1 is a broken perspective view, partly schematic, illustrating a high intensity focused ultrasound stimulation or ablation assembly for use in the methods of the present invention.

FIG. 2 is a broken bottom view of an ultrasound emitting member of a focused ultrasound ablation device of the high intensity focused ultrasound stimulation or ablation assembly.

FIG. 3 is a broken side view, partly in section, of the ultrasound emitting member and depicting focusing of ultrasound energy in the skin to form an ablated tissue area containing unablated skin tissue and a plurality of lesions at which the skin tissue is ablated.

FIG. 4 is a broken top view illustrating the surface or cross-sectional configuration of the ablated tissue area of FIG. 3.

FIG. 5 is a broken top view illustrating the surface or cross-sectional configuration of an alternative ablated tissue area created in the skin.

FIG. 6 is a broken top view illustrating the surface or cross-sectional configuration of a plurality of further alternative ablated tissue areas created in the skin.

FIG. 7 is a broken top view illustrating the surface or cross-sectional configuration of another alternative ablated tissue area created in the skin.

FIG. 8 is a broken bottom view of an alternative focused ultrasound ablation device having a modified ultrasound emitting member for use in the methods of the present invention.

FIG. 9 is a broken top view illustrating the surface or cross-sectional configuration of an additional alternative ablated tissue area formed in the skin.

DESCRIPTION OF THE PREFERRED EMBODIMENTS

A high intensity focused ultrasound ablation or stimulation assembly or system 10 for use in the methods of the present invention is illustrated in FIG. 1 and is similar to the high intensity focused ultrasound stimulation assembly described in parent U.S. patent application Ser. No. 09/487,705 now abandoned and prior U.S. patent application Ser. No. 09/487,710, the disclosures of which are incorporated herein by reference. The high intensity focused ultrasound ablation or stimulation assembly 10 includes a focused ultrasound ablation or stimulation device 12, a power supply 14 and a controller 16. The focused ultrasound ablation or stimulation device 12 is similar to that described in U.S. patent applications Ser. Nos. 09/487,705 now abandoned and 09/487,710 and includes a focused ultrasound emitting member 18, an elongate handle shaft or body 20 having a distal end at which the ultrasound emitting member is disposed and a handle or handpiece 22 coupled to a proximal end of the handle shaft 20. As shown in FIGS. 2 and 3, the ultrasound emitting member includes a transducer 24 carried by or within a housing, carrier or case 26. The transducer, which includes one or more individual ultrasound emitting elements or transducer elements, is capable of generating and emitting ultrasound energy in response to being supplied with electrical power from power supply 14. In the case of ultrasound emitting member 18, the transducer includes a plurality of individual ultrasound emitting elements or transducer elements 28, each including a piezoelectric element that vibrates to produce ultrasound energy when an electrical current or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration causing the ultrasound energy generated thereby to be focused, as shown by arrows in FIG. 3, at focusing zones F, respectively.

The transducer elements 28 are arranged in an array on or in housing 26; and, therefore, the transducer 24 may be considered a multi-array transducer. In the case of ultrasound emitting member 18, the transducer elements are arranged in a planar array of three rows R and six columns C, although the transducer elements can be arranged in any number of rows and columns. In the case of focused ultrasound emitting member 18, each row R has an equal number of transducer elements, and each column C has an equal number of transducer elements. It should be appreciated that any number of transducer elements can be provided in each row and column and that the number of transducer elements provided in each row and column can be the same or different.

The transducer elements 28 can be referenced by their location in the array. For example, the transducer element 28' in the first row, first column can be designated transducer element R1C1, the transducer element 28" in the first row, second column can be designated transducer element R1C2 and so on. The transducer elements may be disposed as close as possible to one another; however, it should be appreciated that the spacing between the individual transducer elements 28 of the array can vary so that adjacent transducer elements can be disposed closer together or further apart from one another. As explained further below, the transducer elements 28 are selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external lower or bottom surface 32 of housing 26. The piezoelectric elements are curved in a direction inwardly of surface 32 such that ultrasound energy generated by the piezoelectric elements is emitted from focused ultrasound emitting member 18 in a direction perpendicular to surface 32 for focusing at the focusing zones F, which are spaced outwardly of surface 32. Accordingly, surface 32 is an active surface or face of the ultrasound emitting member which, when positioned externally on, adjacent or in contact with skin S, results in the ultrasound energy emitted by the transducer being focused at zones F, which will be disposed within the skin S as shown in FIG. 3. When the ultrasound emitting member is positioned on, against or adjacent the skin S at a location aligned with a designated target area 34 within the skin S, the target area 34 being shown in dotted lines in FIGS. 3 and 4, the focusing zones will be disposed at or within the target area as best shown in FIG. 3.

Each focusing zone F consists of a single point or a plurality of points forming a zone at which the ultrasound energy is focused. Each focusing zone is in line with a central axis of the corresponding transducer element. Each focusing zone is disposed a fixed predetermined distance from a plane containing the active face 32, the predetermined distance for each focusing zone being perpendicular or normal to the active face 32. Therefore, the focusing zones F will also be disposed a predetermined perpendicular distance or a calculable or determinable perpendicular distance from an external surface 36 of skin S with which the active face 32 is placed in contact or adjacent thereto. Where the active face 32 is placed in contact with the external skin surface 36, the perpendicular distance that zones F are disposed from external skin surface 36 will be the same as the predetermined distance. Where the active face 32 is not placed in contact with the external skin surface 36 but, rather, is spaced from the external skin surface 36 by a known amount, for example, the perpendicular distance that zones F are disposed from the external skin surface will correspond to the predetermined distance minus the distance that the active face 32 is spaced from the external skin surface 36. Where the active face 32 is spaced from the external skin surface 36, an acoustic coupling medium can be disposed between the external skin surface 36 and the member 18.

Since the ultrasound is focused at focusing zones F, which are spaced from one another, the ultrasound is of greater or higher intensity at focusing zones F than in tissue surrounding the focusing zones F. Ultrasound energy is thusly focused or concentrated at the focusing zones F, causing the skin at the focusing zones F to be heated to an ablative temperature resulting in formation of lesions 38 at the focusing zones, respectively. The tissue is ablated at the lesions 38; and, as used herein, "ablated" tissue includes tissue that has been thermally damaged, altered, necrotized, denatured, destroyed, coagulated or cauterized. When all of the transducer elements 28 are actuated, as shown in FIG. 3, heating of skin S will occur at a focusing zone F for each transducer element, resulting in formation of a lesion 38 at each focusing zone F. The cross-sectional size of the lesions will normally depend on the width of the focusing zones. However, depending on the intensity and duration of the ultrasound energy, the lesions 38 may "grow" or "spread" somewhat beyond the focusing zones due to thermal conduction causing the dispersal or spread of heat from the focusing zones. Therefore, depending on procedural parameters and the dimensions of the focusing zones, each lesion 38 has a predetermined or predictable cross-sectional size, i.e. length and width, as well as depth. As an example, each lesion 38 spreads radially outwardly somewhat from the corresponding focusing zone. The lesions 38 have a generally circular surface or cross-sectional configuration as shown in FIGS. 3 and 4 and a specific depth as shown in FIG. 3. Depending on procedural parameters, the dimensions of the focusing zones and/or the type of tissue being ablated, the lesions may or may not have a uniform cross-section along their depth. Where the focusing zones are sufficiently close together, and where the intensity of the ultrasound energy emitted from the transducer elements is sufficiently high and is applied to the tissue for a sufficient duration, the individual lesions may merge to form a single continuous lesion at the target area so that the target area is filled with ablated tissue. However, depending on the spacing between the focusing zones, and depending on the intensity of the ultrasound energy emitted from the transducer elements and the duration of ultrasound energy delivery to the tissue, the lesions 38 may remain separate, discrete and not connected to one another as shown in FIGS. 3 and 4 so that the target area 34 contains unablated skin tissue and the lesions 38 at which the tissue of the skin is ablated. FIG. 4 illustrates a lesion 38 formed in skin S for each focusing zone F wherein the lesions 38 are disposed within the target area 34 but do not merge with, contact, overlap or abut one another. Rather, each lesion 38 is surrounded or circumscribed perimetrically by unablated skin tissue. The non-contacting lesions 38 and unablated skin tissue are contained in an ablated tissue area 35 at, coincident, coextensive or aligned with the target area 34.

When all of the transducer elements 28 are actuated, an ablated tissue area of specific surface or cross-sectional configuration and size is created within the skin S for the transducer 24 in accordance with the configuration and size of the array, the intensity level of the emitted ultrasound energy, the duration or time of ultrasound energy delivery to the skin, and the size of the lesions. Accordingly, an ablated tissue area having a specific cross-sectional length, width and depth is formed in the skin, with the perimeter of the ablated tissue area circumscribing the array of lesions 38. FIGS. 3 and 4 illustrate, in dotted lines, the ablated tissue area 35 formed in skin S when all of the transducer elements are actuated. The ablated tissue area 35 has a generally rectangular surface or cross-sectional configuration or area with a predetermined cross-sectional length and width shown in FIG. 4 and a predetermined cross-sectional depth, shown in FIG. 3, the cross-sectional depth corresponding to the depth of the lesions 38. When the ultrasound emitting member 18 is positioned on, against or adjacent the skin S at a location aligned with a designated target area 34 in the skin, the ablated tissue area 35 will be formed at or coincide with the target area as shown in FIGS. 3 and 4. The ablated tissue area is surrounded, bordered or circumscribed perimetrically by unablated skin tissue, as well as having unablated skin tissue above and below it. Since the focusing zones F begin the predetermined distance or the calculable or determinable distance below the external skin surface 36, the ablated tissue area 35 is an internal or subsurface ablated tissue area beginning the predetermined distance or the calculable or determinable distance beneath the external skin surface. Accordingly, the lesions 38 and ablated tissue area 35 begin at a beginning or starting margin 64 located the predetermined or calculable distance below the external tissue surface 36 and end at an ending margin 66 disposed further below the external tissue surface than the beginning margin, the distance between the beginning and ending margins corresponding to the depth of the lesions 38 and, therefore, the depth of the ablated tissue area 35.

The housing 26 can have various external configurations and sizes and can be formed by a portion of the transducer or can mount the transducer elements in various ways. The handle shaft 20 comprises an elongate, hollow or tubular member of sufficient length to position the ultrasound emitting member 18 at various operative sites in or on the body of a patient while the handle 22 is maintained at a remote location, typically externally of the patient's body. The handle shaft 20 could be solid and may comprise a bar or other shaped member. Preferably, the handle shaft 20 is malleable as disclosed in U.S. patent application Ser. No. 09/488,844 now U.S. Pat. No. 6,361,531 issued Mar. 26, 2002, the disclosure of which is incorporated herein by reference. The handle 22 has a forward end coupled to the proximal end of handle shaft 20 and has a rearward end. The handle 22 preferably has a configuration to facilitate grasping by a surgeon or other operator. One or more controls or switches 42 may be provided on handle 22 to effect operation of the focused ultrasound ablation device.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include an RF generator, with or without an amplifier, providing a constant current source. Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 42 on the handle.

In the case of focused ultrasound ablation device 12, a transmission wire 44 is provided for each piezoelectric element and, therefore, for each transducer element. As shown in FIG. 3, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. However, the transmission wires can be disposed externally of the housing and/or the shaft. The transmission wires 44 are connected to switches (not shown), respectively, for controlling the supply or transmission of current from the power supply 14 to the piezoelectric elements, respectively. The switches can be incorporated in the ultrasound emitting member 18, the power supply 14 and/or the controller 16.

The controller or control unit 16 controls the supply of power from power supply 14 to transducer 24 so that the transducer can be driven to deliver various intensity levels of ultrasound energy for various durations, periods or lengths of time. In particular, the controller 16 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other non-selected transducer elements can remain deactivated to prevent transmission of electrical current thereto when the power supply is actuated or switched to an "on" mode. It should be appreciated that various components and/or methodology can be incorporated in the device 12, the power supply 14 and/or the controller 16 to permit selective actuation of selected ones of the transducer elements 28 and that such components and/or methodology would be within the purview of one skilled in the art.

Various transducers can be used in the methods of the present invention. The piezoelectric elements can be made of various piezoelectric materials such as PZT crystal materials, hard lead, zirconate/lead titanium, piezoelectric ceramic, or lithium-niobate piezoceramic material. The transducer elements can be of various sizes and can have various focusing geometries. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of the skin to be effected in response to the application or delivery of ultrasound energy to the skin for a relatively short duration or length of time. In accordance with the present invention, the duration or length of time for ultrasound energy delivery or application to the skin preferably ranges from 2 to 60 seconds depending on desired lesion size and/or ablative effect.

In accordance with the methods of the present invention, high intensity focused ultrasound is used to create an internal ablated tissue area within the skin containing unablated skin tissue and a plurality of lesions at which the tissue of the skin is ablated. In reaction to the lesions, collagen growth in the skin is stimulated. In this manner, collagen levels in the skin are increased resulting in a reduction of wrinkles, enhanced skin resilience and a more youthful appearance.

The skin S, as shown in FIG. 3, includes an outer or external layer, known as the epidermis E, and an inner or internal layer, known as the dermis DE. The epidermis E is comprised of a plurality of sub-layers including several layers of stratified epithelial tissue and defines external skin surface 36. The epidermis E has a basilar layer including melanocytes, which produce melanin serving to protect the skin from the harmful effects of ultraviolet radiation. The dermis DE, or "true skin", is comprised of connective tissue with a varying amount of elastic fibers and numerous blood vessels, lymphatics, nerves and hair follicles H. The dermis DE includes a superficial layer, known as the superficial dermis or papillary layer L, and a deep layer, known as the deep dermis or reticular layer R. The superficial layer L may itself be considered as comprising a plurality of superficial sub-layers forming the superficial dermis. The reticular layer R contains collagen C and elastin, which impart firmness, flexibility and durability to the skin.

As shown in FIG. 3, the ultrasound emitting member 18 is placed against the skin S of a patient to position the active face 32 in contact with the external skin surface 36. The active face is placed at or on the skin surface 36 at a location aligned with a desired target area 34 in the skin for creation of an ablated tissue area, such location corresponding to an area of the skin that is to be rejuvenated. The shaft 20 may be grasped and manipulated, as necessary, to facilitate positioning of the active face at the desired location on the external skin surface. Typically, the ultrasound emitting member will be placed in contact with skin of the patient's face at a location where a reduction in wrinkles is desired, such as the forehead, cheeks, and the areas around the mouth and eyes. Also, all or specific ones of the transducer elements are selected for actuation or "firing" in accordance with the desired size and configuration for the ablated tissue area and/or the desired number of lesions to be contained in the ablated tissue area. The ablation device 12 is programmed via the controller to effect actuation or "firing" of the selected transducer elements when electric current or a signal is supplied to the transducer. Of course, selection and programming for actuation or "firing" of selected transducer elements can be perfomed prior to positioning of member 18 on the skin surface.

Once the active face is positioned in contact with the skin S at the desired location, the power supply is activated or switched to an "on" mode to transmit electrical energy to the previously selected transducer elements. In response thereto, the piezoelectric elements corresponding to the selected transducer elements vibrate and produce ultrasound energy, which is focused within the skin S at the corresponding focusing zones F. In the procedure of FIG. 3, all of the transducer elements are "fired" to emit ultrasound energy, causing the skin to be heated to an ablative temperature at a focusing zone for each transducer element. The skin S at the focusing zones is heated to a temperature in the range of 60 to 90 degrees Celsius for the time required to achieve ablation or thermal damage in the skin. The focusing zones are contained in the target area 34, which is coincident with or disposed in the superficial dermis L and is thusly disposed between the epidermis E and the deep dermis R. The skin S is heated at the focusing zones to a sufficiently high temperature so as to cause a plurality of subsurface or internal lesions 38 to be simultaneously formed in the skin S and, in particular, in the superficial dermis L, while the ultrasound emitting member 18 remains external of and does not physically penetrate the skin S.

Lesions 38 have a generally circular surface or cross-sectional configuration as shown in FIGS. 3 and 4 and do not contact or touch one another. Lesions 38 contain ablated or damaged skin tissue while the skin tissue surrounding each lesion 38 is not heated to the ablative or thermally damaging temperature and, therefore, is unablated or undamaged. In this manner, eighteen discontinuous or non-contacting individual lesions 38 are formed in the skin as represented in FIG. 4. Lesions 38 are contained in the internal ablated tissue area 35 coincident with the target area 34, the ablated tissue area 35 containing the lesions 38 and the unablated skin tissue between adjacent lesions 38. The lesions 38 have a cross-sectional length and width and a depth of known parameters depending on the size and focusing geometry of the transducer elements, the intensity of the ultrasound energy, the temperature to which the skin is heated and the duration of ultrasound energy delivery or application to the skin.

Due to the predetermined distance and the known length for the focusing zones, the lesions 38 and, therefore, the ablated tissue area 35, begin at the beginning or starting margin 64 located a predetermined or known depth beneath or below the external skin surface 36 and end at the ending margin 66 located a greater predetermined or known depth beneath the external skin surface 36, the distance between the beginning and ending margins corresponding to the depth of the lesions and, therefore, the depth of the ablated tissue area 35. By selecting the appropriate focusing zone depth and treatment parameters, a desired thickness or depth of unablated or undamaged skin tissue between the beginning margin 64 and the external tissue surface 36 is disposed outside the ablated tissue area. Preferably, the beginning margin is located 50 to 150 micrometers below the external skin surface. In the method of FIGS. 3 and 4, a layer of unablated skin tissue about 100 micrometers thick is maintained between the external skin surface 36 and the beginning or starting margin 64 of the lesions 38, thusly preserving the epidermis E of the skin S. The lesions 38 have a depth of 50 to 150 micrometers and, preferably, a depth of about 100 micrometers, in the direction perpendicular to skin surface 36 such that the ablated tissue area and the lesions terminate or end at the ending margin 66 disposed a depth of about 200 micrometers beneath the external skin surface 36 at the transducer/tissue interface. Accordingly, there is a perpendicular distance of about 200 micrometers from the external skin surface to the ending margin of the ablated tissue area such that the deep dermis R is undamaged and preserved. By selecting the appropriate focusing zone length and treatment parameters, the depth of the ending margin 66 within the skin is controlled thusly ensuring that the ablated tissue area and lesions do not extend or extend only an insignificant amount into the deep dermis.

As shown in FIG. 4, the ablated tissue area 35, which is surrounded above, below and perimetrically by unablated or undamaged skin tissue, has a surface or cross-sectional configuration or area of generally rectangular shape with a cross-sectional width and length varying from 3 mm to 50 mm in either dimension, i.e. 3 mm×3 mm to 50 mm×50 mm or in between, depending on the size of the area to be treated. Although the cross-sectional length and width or other external dimensions of the ablated tissue area can be determined by the locations of the "fired" transducer elements, it should be appreciated that the cross-sectional length and/or width of the ablated tissue area can alternatively be obtained by moving the member 18 along the skin as described in U.S. patent application Ser. No. 09/487,705, the disclosure of which is incorporated herein by reference.

Depending on the desired lesion size and/or thermal effect, ultrasound energy will be delivered or applied to the skin for a duration in the range of 2 to 60 seconds. The emission of ultrasound energy by ultrasound emitting member 18 is terminated by the surgeon or other operator once lesions of desired size or a desired amount of tissue ablation has been obtained, and the member 18 is removed from the patient's skin. In order to terminate the emission of ultrasound energy by the ultrasound emitting member, the power supply is deactivated or switched to an "off" mode so that electrical current is no longer supplied to the selected piezoelectric elements.

The lesions 38, which typically contain thermally damaged tissue, cause the dermis DE to be stimulated to produce collagen C in the vicinity of the lesions. The lesions 38 are naturally assimilated or degraded and absorbed by the patient's body and are replaced by healthy skin tissue. Accordingly, the level of collagen in the patient's skin increases in the vicinity of the lesions resulting in a reduction of wrinkles, greater resiliency and a more youthful appearance.

FIG. 5 is representative of a single treatment procedure in accordance with the present invention wherein a subsurface ablated tissue area 135 containing four non-contacting lesions 138 is formed in the skin S. The ablated tissue area 135 is similar to ablated tissue area 35 except that it is of generally square surface or cross-sectional configuration or area and contains four generally circular lesions 138 each surrounded by unablated skin tissue. The ablated tissue area 135 can be formed using the ultrasound emitting member 18 by selecting and "firing" transducer elements R1C1, R1C2, R2C1 and R2C2, for example, to emit ultrasound energy. As described for the procedure illustrated in FIGS. 3 and 4, the ultrasound energy emitted by the selectively "fired" or actuated transducer elements is focused in the skin at a focusing zone for each actuated transducer element, causing subsurface lesions 138 to be formed in the skin at the focusing zones corresponding to transducer elements R1C1, R1C2, R2C1 and R2C2. The lesions 138 are similar to lesions 38 but are larger in diametric cross-sectional size than lesions 38. The ablated tissue area 135 is surrounded by unablated tissue above, below and perimetrically.

FIG. 6 is representative of a multiple treatment procedure in accordance with the present invention wherein a plurality of internal ablated tissue areas 235, each containing unablated skin tissue and a plurality of lesions 238, are formed or created in the skin S. The ablated tissue areas 235 are spaced from one another, and each contains two generally circular lesions 238 similar to lesions 138 except that lesions 238 have a slightly larger cross-sectional diameter than lesions 138. The lesions 238 of each ablated tissue area 235 are spaced slightly from one another and are surrounded by unablated skin tissue so as to be non-contacting. Each ablated tissue area 235 has a surface or cross-sectional configuration or area of generally rectangular shape. The ablated tissue areas 235, which are similar to ablated tissue area 35 except for their cross-sectional configuration, can be formed using member 18 as described above by actuating an appropriate pair of transducer elements. The ablated tissue areas 235 are typically formed in separate treatments performed at different times. However, it should be appreciated that a plurality of ablated tissue areas, such as ablated tissue areas 235, can be formed in the skin during a single procedure performed at one time.

FIG. 7 illustrates in dotted lines an ablated tissue area 335 of rectangular cross-sectional configuration formed in the skin S and containing six generally circular non-contacting lesions 338 each surrounded by unablated tissue. The lesions 338 and ablated tissue area 335 are similar to the lesions 38 and ablated tissue area 35 except for the cross-sectional size of lesions 338 being different from the cross-sectional size of lesions 38. The ablated tissue area 335 will typically be formed in a single treatment or procedure. The ablated tissue area 335 can be formed using the ultrasound emitting member 18 by actuating six appropriate transducer elements.

It should be appreciated that the methods of skin rejuvenation according to the present invention can be performed using focused ultrasound ablation devices wherein the transducer elements of the ultrasound emitting members are not selectively actuatable. For example, FIG. 8 illustrates an alternative focused ultrasound ablation device 412 having focused ultrasound emitting member 418, which is similar to focused ultrasound emitting member 18 except that focused ultrasound emitting member 418 includes an array of six transducer elements 428 actuatable simultaneously or in unison to emit ultrasound energy. The transducer elements 428 are arranged in two rows and three columns and are used to form an ablated tissue area containing six lesions, such as ablated tissue area 335. Accordingly, it should be appreciated that various dedicated ultrasound emitting members having different arrays and/or numbers of transducer elements can be provided, with a particular ultrasound emitting member being capable of obtaining a particular ablated tissue area of predetermined size, configuration and number of lesions in response to actuation of all of the transducer elements of the particular ultrasound emitting member.

FIG. 9 illustrates an alternative, subsurface ablated tissue area 535 formed in the skin S in a manner similar to ablated tissue area 135. However, the ultrasound energy used to form ablated tissue area 535 is of higher intensity and/or is applied to the skin for a longer duration than the ultrasound energy used to form ablated tissue area 135. Accordingly, the lesions 538 of ablated tissue area 535 have a generally circular surface or cross-sectional configuration larger in diameter than the generally circular cross-sectional configuration of lesions 138 due to greater dispersal of heat from the focusing zones. As a result, the lesions 538 contact or touch one another but still do not merge sufficiently to fill the entire ablated tissue area 535 with ablated tissue. Although each lesion 538 is not completely surrounded perimetrically by unablated tissue, there is still some unablated tissue within the ablated tissue area 535 as shown in FIG. 9 by unablated skin tissue disposed between adjacent lesions 538. It should be appreciated, therefore, that the ablated tissue areas formed in accordance with the present invention can include a plurality of non-contacting lesions each completely surrounded by unablated tissue and/or a plurality of contacting lesions with unablated tissue between the contacting lesions.

In the procedures described and illustrated above, the ultrasound emitting member is placed against the skin at a desired location to form an ablated tissue area of final size and configuration in the skin with focused ultrasound energy generated and emitted by the ultrasound emitting member without moving the ultrasound emitting member from the desired location. It should be appreciated, however, that where the largest size ablated tissue area capable of being formed in the skin with the ultrasound emitting member is smaller than the final size and/or different from the final configuration desired for the ablated tissue area, the ultrasound emitting member can be moved along the skin to form an ablated tissue area of desired final size and configuration as explained in U.S. patent application Ser. No. 09/487,705 now abandoned.

The methods of the present invention allow skin rejuvenation to be performed with minimal trauma and pain for the patient and with faster healing and recovery times. The epidermis is preserved so that no external wound is presented or exposed. A single treatment in accordance with the present invention may be sufficient to reduce wrinkles in a desired area since an ablated tissue area of sufficient size may be obtained with a single treatment. By controlling the delivery of ultrasound energy to the skin, the temperature to which the skin is heated by the ultrasound energy can be controlled to avoid undesired patient responses. The ultrasound emitting members can be provided with sensors for monitoring the amount of ultrasound energy delivered to the skin and/or for detecting the temperature to which the skin is heated, which can be provided as feedback to the controller. The delivery of ultrasound energy to the skin can be controlled to achieve a selected temperature in the skin, a selected amount of ablation, a desired lesion size or a desired duration of ultrasonic energy delivery. The ultrasound emitting members can be disposable or can be designed to be reusable and thusly can be capable of being sterilized to medical standards. The ultrasound emitting members can be provided with disposable covers or guards which can be removed and discarded after use so that the ultrasound emitting members can be reused. The transducer or transducer elements can be removable from the ultrasound emitting members allowing disposability of the ultrasound emitting members and reuse of the transducer or transducer elements in another ultrasound emitting member. The ultrasound emitting members can be immobilized during use as may be accomplished with various types of stabilizing members provided on the shafts or on the ultrasound emitting members. The focused ultrasound ablation devices can be provided with imaging capabilities or can be used with various imaging devices as disclosed in U.S. patent application Ser. No. 09/487,705 now abandoned. The focused ultrasound ablation devices can be provided with cooling systems for cooling the ultrasound emitting members and/or the transducers as disclosed in U.S. patent application Ser. No. 09/487,705 now abandoned. The methods of skin rejuvenation can be performed using an acoustic coupling medium as disclosed in U.S. patent application Ser. No. 09/487,705 now abandoned. A single ultrasound emitting member can be used to form various different ablated tissue areas of various sizes, configurations, and number of lesions depending on the particular transducer elements selected for actuation. A plurality of different ultrasound emitting members having non-selectively actuatable transducer elements can be provided with each ultrasound emitting member having a different array and/or number of transducer elements to obtain a particular ablated tissue area of predetermined size, configuration and number of lesions when all of the transducer elements of the ultrasound emitting members are actuated. Any number of ablated tissue areas can be formed in the skin with each ablated tissue area surrounded by unablated tissue or with the ablated tissue areas contiguous to, in abutment with, contacting or overlapping one another to form a single ablated tissue area. The ultrasound emitting members, the transducers and/or the transducer elements can be moved relative to the tissue to scan target areas with focused ultrasound energy, and such scanning can be accomplished in various diverse ways. The ablated tissue areas can include unablated tissue and a plurality of non-contacting lesions, a plurality of contacting lesions or a combination of contacting and non-contacting lesions. Any number of lesions can be contained in the ablated tissue areas including even and odd numbers of lesions.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of skin rejuvenation comprising the steps of
positioning an ultrasound emitting member adjacent an external tissue surface of the skin of a patient;
emitting ultrasound energy from the ultrasound emitting member into the skin;
focusing the ultrasound energy simultaneously at a plurality of spaced focusing zones contained in a target area in the skin;
heating the skin at the focusing zones with the focused ultrasound energy to form an ablated tissue area at the target area containing unablated tissue of the skin and a plurality of lesions at the focusing zones, respectively, at which the tissue of the skin is ablated; and
removing the ultrasound emitting member from adjacent the external surface of the skin.

2. The method of skin rejuvenation as recited in claim 1 wherein said step of focusing includes focusing the ultrasound energy in a target area disposed beneath the external surface of the skin.

3. The method of skin rejuvenation as recited in claim 2 wherein said step of heating includes heating the skin at the focusing zones with the focused ultrasound energy to achieve a temperature in the range of 60 to 90 degrees Celsius.

4. The method of skin rejuvenation as recited in claim 3 wherein said step of heating includes heating the skin at the focusing zones with the focused ultrasound energy so that the lesions begin at a beginning margin located below the epidermis of the skin.

5. The method of skin rejuvenation as recited in claim 4 wherein said step of heating includes heating the skin at the focusing zones with the focused ultrasound energy so that the lesions end at an ending margin located above the deep dermis of the skin.

6. The method of skin rejuvenation as recited in claim 5 wherein said step of heating includes heating the skin at the focusing zones with the focused ultrasound energy for a duration in the range of 2 to 60 seconds.

7. The method of skin rejuvenation as recited in claim 1 wherein said step of heating includes forming the ablated tissue area surrounded by unablated tissue of the skin.

8. The method of skin rejuvenation as recited in claim 7 wherein said step of heating includes forming the ablated tissue area so that the plurality of lesions do not contact one another.

9. The method of skin rejuvenation as recited in claim 7 wherein said step of heating includes forming the ablated tissue area so that at least one of the plurality of lesions contacts another of the plurality of lesions.

10. A method of skin rejuvenation comprising the steps of
positioning an ultrasound emitting member adjacent an external surface of the skin;
emitting ultrasound energy simultaneously from a plurality of ultrasound emitting elements of the ultrasound emitting member;
focusing the ultrasound energy in the skin below the external surface of the skin at a plurality of spaced focusing zones corresponding to the ultrasound emitting elements, respectively, while the ultrasound emitting member is maintained in one place adjacent the external surface of the skin;
ablating the skin with the focused ultrasound energy to form an ablated tissue area below the external surface of the skin containing unablated tissue of the skin and a plurality of lesions at the focusing zones, respectively, at which the tissue of the skin is ablated, the reaction to which is production of collagen by the dermis; and
removing the ultrasound emitting member from adjacent the external surface of the skin.

11. The method of skin rejuvenation as recited in claim 10 wherein said step of ablating includes forming the plurality of lesions to begin at a beginning margin located 50 to 100 micrometers below the external surface of the skin.

12. The method of skin rejuvenation as recited in claim 11 wherein said step of ablating includes forming the plurality of lesions to have a depth of 50 to 150 micrometers.

13. The method of skin rejuvenation as recited in claim 12 wherein said step of ablating includes forming the ablated tissue area to have a cross-sectional length of 3 to 50 mm and a cross-sectional width of 3 to 50 mm.

14. The method of skin rejuvenation as recited in claim 10 wherein said step of focusing includes focusing the ultrasound energy in the superficial dermis of the skin.

15. A method of skin rejuvenation comprising the steps of
positioning an ultrasound emitting member adjacent an external surface of the skin of a patient;
actuating selected ones of a plurality of ultrasound emitting elements of the ultrasound emitting member to emit ultrasound energy;
simultaneously emitting ultrasound energy from the selected ultrasound emitting elements into the skin;
focusing the ultrasound energy in the skin below the epidermis simultaneously at a plurality of spaced focusing zones corresponding to the selected ultrasound emitting elements, respectively;
ablating the skin with the focused ultrasound energy to form an ablated tissue area below the epidermis containing unablated tissue of the skin and a plurality of lesions at the focusing zones, respectively, at which the tissue of the skin is ablated; and
removing the ultrasound emitting member from adjacent the external surface of the skin.

16. The method of skin rejuvenation as recited in claim 15 and further including, prior to said step of actuating, the step of selecting the ultrasound emitting elements to be actuated in accordance with a desired surface pattern for the plurality of lesions.

17. The method of skin rejuvenation as recited in claim 16 wherein said step of ablating includes forming the ablated tissue area between the epidermis and deep dermis of the skin.

18. The method of skin rejuvenation as recited in claim 15 and further including, subsequent to said step of removing, the step of allowing the plurality of lesions to be assimilated by the patient's body whereby the production of collagen by the skin is increased in the ablated tissue area.

* * * * *